United States Patent
Dorfman

(10) Patent No.: US 6,923,761 B1
(45) Date of Patent: Aug. 2, 2005

(54) RETRACTORS

(75) Inventor: William Dorfman, Granada Hills, CA (US)

(73) Assignee: Discus Dental Impressions, Inc., Culver City, CA (US)

( * ) Notice: Subject to any disclaimer, the term of this patent is extended or adjusted under 35 U.S.C. 154(b) by 234 days.

(21) Appl. No.: 10/371,665

(22) Filed: Feb. 21, 2003

Related U.S. Application Data

(63) Continuation-in-part of application No. 29/172,164, filed on Dec. 6, 2002, now Pat. No. Des. 496,995.

(51) Int. Cl.[7] .............................................. A61B 1/32
(52) U.S. Cl. ..................................... 600/237; 433/140
(58) Field of Search ............................... 600/206, 208, 600/210, 216, 235, 236, 237, 238, 239, 242; 433/6, 7, 91, 93, 94, 136, 137, 138, 139, 433/140, 141; 128/862

(56) References Cited

U.S. PATENT DOCUMENTS

| | | |
|---|---|---|
| 1,170,333 A | 2/1916 | Reyer |
| 1,474,497 A | 11/1923 | Stolper |
| 2,859,519 A | 11/1958 | Cohn |
| 3,241,550 A | 3/1966 | Gelarie |
| 3,916,880 A | 11/1975 | Schroer |
| 4,002,162 A | 1/1977 | Weisser |
| 4,019,255 A | 4/1977 | Cohen et al. |
| 4,053,984 A | 10/1977 | Moss |
| 4,200,089 A | 4/1980 | Inoue |
| 4,511,329 A | 4/1985 | Diamond |
| 4,671,260 A | 6/1987 | Buckner |
| 4,889,491 A | 12/1989 | Krygier et al. |
| 5,037,298 A | 8/1991 | Hickham |
| 5,570,704 A * | 11/1996 | Buzzard et al. ............. 128/848 |
| 5,718,240 A * | 2/1998 | Dunlop ....................... 128/859 |
| 5,873,718 A | 2/1999 | Sullivan |
| 6,102,701 A | 8/2000 | Engeron |
| 6,203,471 B1 * | 3/2001 | Akihiro ....................... 482/11 |
| 6,743,017 B2 * | 6/2004 | O'Neill ....................... 433/140 |

* cited by examiner

Primary Examiner—Eduardo C. Robert
Assistant Examiner—Annette Reimers
(74) Attorney, Agent, or Firm—Christie, Parker & Hale, LLP

(57) ABSTRACT

Retractors discussed herein include lip retractors that have four channel retainers to retain four portions of the lips. The four channel retainers are attached to four resilient members, which are adapted to bias the four channel retainers outwardly away from one another, which in turn retract the portions of the lips that are retained by the four channel retainers to expose the teeth and/or mouth. Optionally, the retractors may be equipped with a tongue retainer. If equipped, the tongue retainer is adapted to limit the tongue to further expose the backside of the teeth.

21 Claims, 7 Drawing Sheets

RETRACTORS

CROSS-REFERENCE TO RELATED APPLICATION

This is a continuation in part of application Ser. No. 29/172,164, filed on Dec. 6, 2002, now U.S. Design Patent No. D496,995.

Retractors for retracting the lips are generally discussed herein with specific discussion to retractors for retracting portions of the upper and lower lips, and optionally the tongue, to expose the teeth and/or the mouth area for examination and/or treatment.

BACKGROUND

Mouth corner spreading devices, also known as cheek retractors or tongur cups, are well known in the art for spreading portions of the lips, which spread the cheeks, for examination and/or treatment by healthcare professionals. Exemplary mouth corner spreading devices include devices that spread a portion or several portions of the upper and lower lips using levers that are biased apart by an assistant, using flanges that cup and spread the lips, using devices that include metal resilient members, and using devices that have two retaining members for spreading two portions of the lips. However, there is still a need for a retractor as described below for the advantages that are associated therewith.

SUMMARY

According to the present invention, there is provided a retractor for retracting a user's lips comprising four channel retainers or flanges and four resilient members, wherein each channel retainer comprises a race, an inside side wall, and an outside side wall, and wherein each resilient member is integrally molded to two outside side walls of two adjacent channel retainers and comprises an arch.

According to another aspect of the present invention, there is provided a retractor for retracting a user's lips comprising four channel retainers and a tongue retainer, the four channel retainers being held in a spaced apart relationship by four resilient members, and the tongue retainer being attached to two of the channel retainers by two secondary resilient members.

Other alternatives and embodiments for practicing the invention are also described herein and further discussed below in the Detailed Description section.

BRIEF DESCRIPTION OF THE DRAWINGS

These and other features and advantages of the present invention will become appreciated as the same become better understood with reference to the specification, claims and appended drawings wherein:

DETAILED DESCRIPTION

The detailed description set forth below in connection with the appended drawings is intended as a description of the presently preferred embodiments of the retractor provided in accordance with the present invention and is not intended to represent the only forms in which the present invention may be constructed or utilized. The description sets forth the features and the steps for constructing and using the retractor of the present invention in connection with the illustrated embodiments. It is to be understood, however, that the same or equivalent functions and structures may be accomplished by different embodiments that are also intended to be encompassed within the spirit and scope of the invention. Also, as denoted elsewhere herein, like element numbers are intended to indicate like or similar elements or features.

Figure 1:
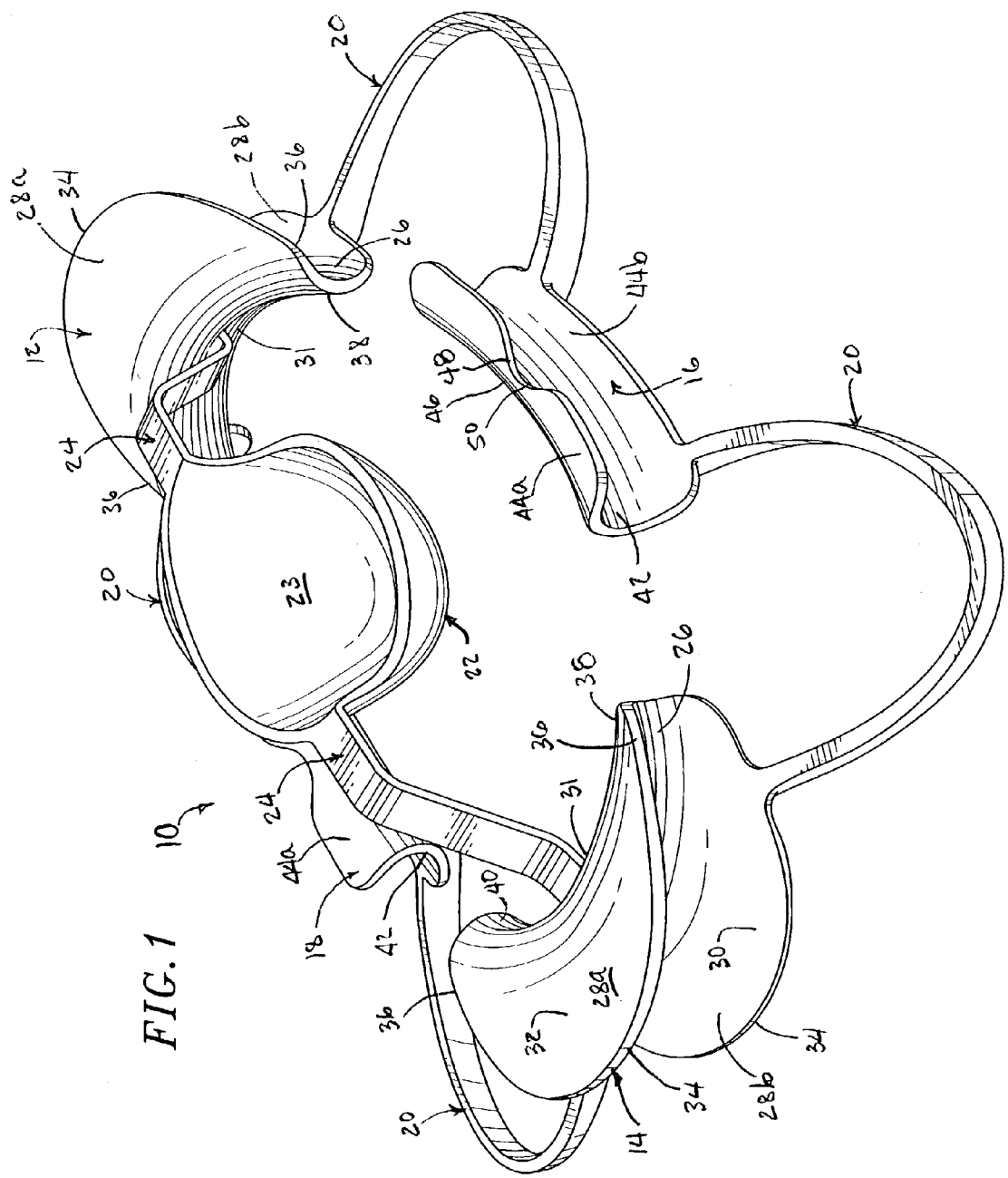
FIG. 1 depicts a semi-schematic perspective view of a retractor provided in accordance to one practice of the present invention.

Referring now to FIG. 1, there is shown a retractor for retracting the upper and lower lips (herein "lips") for facilitating examination and/or treatment of the mouth and/or teeth provided in accordance to one practice of the present invention, which is generally designated 10. The retractor 10, which is also known as a tongue cup, comprises four spaced apart channel retainers 12, 14, 16, 18, also known as flanges, for retaining four corresponding portions of the lips for examination and/or treatment of the mouth or teeth. When used, the retractor 10 draws back the lips, which retracts the cheeks, to expose the mouth so that a health care professional can more easily see the teeth and work on the teeth and/or mouth.

The four channel retainers include two side channel retainers 12, 14 for retaining the ends of the lips, approximately where the upper and the lower lips intersect, and two lip channel retainers 16, 18 for retaining the mid-section of the upper and lower lips. More particularly, the four channel retainers or flanges 12, 14, 16, 18 are adapted to cup the lips and bias them open to expose the teeth for treatment and/or examnination.

A plurality of resilient members 20 are incorporated in the retractor 10 to interconnect the four channel retainers 12, 14, 16, 18 together and to function as biasing means. In the ready position (before insertion of the retractor into the mouth), the resilient members 20 are arched outwardly with respect to the center portion of the retractor 10. As further discussed below, when the retractor 10 is inserted into the mouth and the four channel retainers 12, 14, 16, 18 cup respective portions of the lips, the resilient members 20 provide a retractive force to retract the lips radially outwardly for examination and/or treatment.

An optional tongue retainer 22 is shown approximately centrally positioned relative to the four channel retainers 12, 14, 16, 18. The tongue retainer 22 comprises a trough 23 and is attached to two channel retainers 12, 14 by a pair of secondary resilient members 24. When incorporated, the tongue retainer 22 and the secondary resilient members 24 cooperate to block the tongue and limit the tongue to the back vicinity of the mouth, thus enabling access to the lingual portion or back of the teeth for examination and/or treatment. In short, the tongue retainer is configured to minimize interference by the tongue during treatment and/or examination by a health care professional.

The side channel retainers 12, 14 resemble a curvilinear c-channel in that they include an arcuate race 26 and two channel side walls 28a, 28b. The channel side walls 28a, 28b resemble a bell shape and include a maximum wall dimension at approximately the mid-point 34 and two smaller tapered tips 36 at the ends thereof. In one embodiment, the inside side wall 28a, which is intraoral as further discussed below, is slightly larger relative to the outside side wall 28b. However, the relative dimensions can be reversed or can be the same without deviating from the functionality of the lip retractor 10.

The side channel retainers 12, 14 further include an interior surface 30 and an exterior surface 32. The arcuate race 26 comprises a radius of curvature 31 adapted to mimic the curvature of the side of the lips when the lips are in the opened position. Because this curvature may vary depending on the size and age of the user or patient, the retractor 10 may be implemented with varying radius of curvatures 31 to fit the varied shape of the particular user/patient. The arcuate race 26 may also include an irregular curvature or two or more different radiuses of curvatures. For example, the lower region 38 of the radius of curvature 31 may have a larger radius than the upper region 40 or vice versa. If implemented, the irregular curvature can vary the amount of retraction of the portion of the lip that is seated within the arcuate race to vary the amount of retraction between those portions of the lip. The two lip channel retainers 16, 18 can also have different radiuses of curvatures, similar to the side channel retainers 12, 14.

The lip channel retainers 16, 18, like the side channel retainers 12, 14, resemble a curvilinear c-channel in that they include an arcuate race 42 and two channel side walls 44a, 44b. In one embodiment, the radius of curvature 46 of the lip channel retainers is larger than the radius of curvature 31 of the side channel retainers 12, 14. The larger radius of curvature 46 enables the lip channel retainers 16, 18 to conform to the contour of the upper and lower lips near the frenum, which is more planar relative to the side of the lips. Depending on the size and age of the intended user/patient, the radius of curvature 46 of the lip channel retainer 16, 18 can also vary.

As shown, a frenum release 48 is incorporated in the inside side walls 44a of the lip channel retainers 16, 18 for providing relief to the frenum of the upper and lower lips. In one embodiment, the frenum release 48 comprises a partial oval shaped cutout having a size sufficient to provide clearance for the frenum. In other words, the frenum release 48 should be such that the lowest most portion 50 of the frenum release only slightly touches the frenum when in use, and more preferably not touch the frenum. Although the oval shaped cutout is shown for the frenum release 48, a partial circle, a rectangular cutout, a square cutout, or other geometrical shaped cutout may also be incorporated without deviating from the function of the frenum release. The retractor 10 may be made by injection molding a thermoplastic material such as polypropylene, polyethylene, polystyrene, or the like. More preferably, the retractor 10 is made by injection molding polypropylene and having a smooth and transparent finish.

Figure 2:
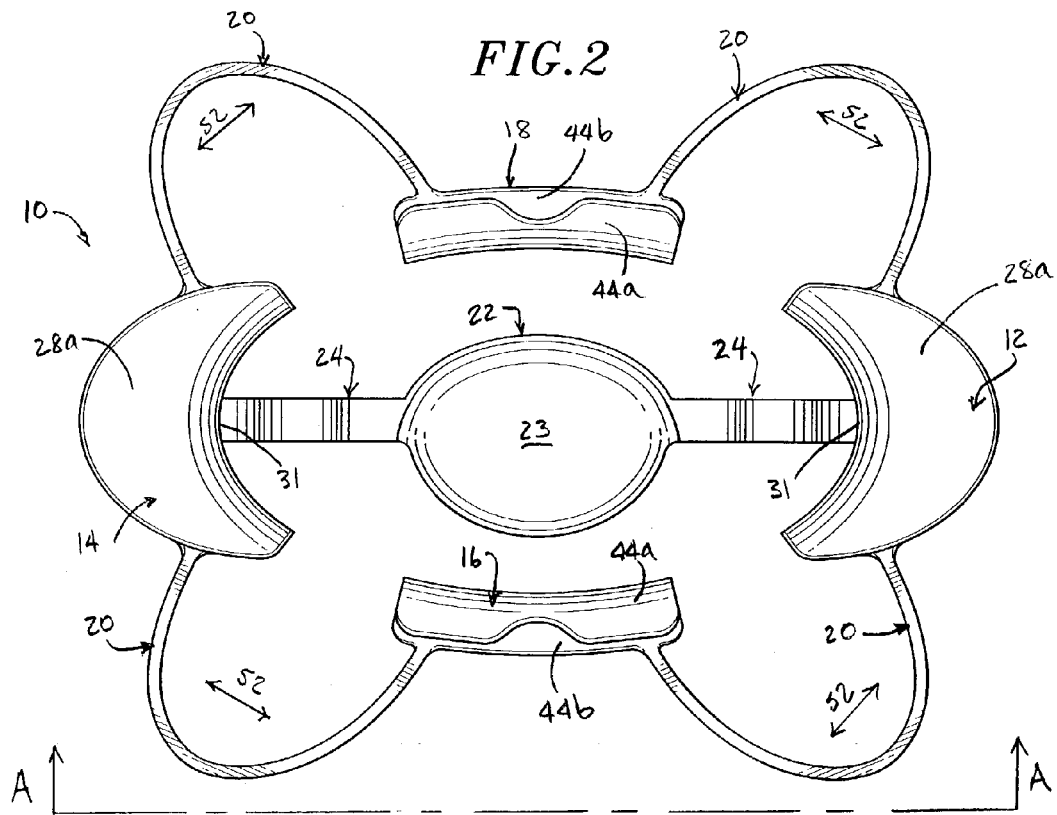
FIG. 2 depicts a semi-schematic bottom plan view of the retractor of FIG. 1.

FIG. 2 is a semi-schematic bottom plan view of the retractor 10 of FIG. 1. FIG. 2 shows the retractor 10 in a ready position, which is the position in which the four resilient members 20 bias the four channel retainers 12, 14, 16, 18 outwardly 52 away or in a spaced relationship from one another. Similarly, the two secondary resilient members 24 bias the tongue retainer 22 away from the plane defining the position of the four channel retainers 12, 14, 16, 18 (approximately perpendicularly towards the viewer). Hence, as further discussed below, when the retractor 10 is placed in the mouth during service, the four channel retainers 12, 14, 16, 18 are adapted to cup the lips and the four resilient members 20 are adapted to spread the lips open due to the resiliency of the resilient members 20 to expose the labial or front portions of the teeth. Similarly, the tongue retainer 22 is adapted to block the tongue and the two secondary resilient members 24 are adapted to limit the tongue to the back region of the mouth, towards the back of the throat, to further expose the lingual or back portions of the upper and lower teeth.

The retractor 10 is configured to fit into the mouth in the orientation shown in FIG. 2. In other words, the inside side walls 28a, 44a, the secondary resilient members 24, and the tongue retainer 22, including the trough 23, are configured to be intraoral while the outside side walls 28b, 44b and the four resilient members 20 are configured to be extraoral. As readily apparent, the four resilient members 20 are integrally molded to the outside side walls 28b, 44b to not interfere with the insertion of the retractor into the mouth.

Figure 3:
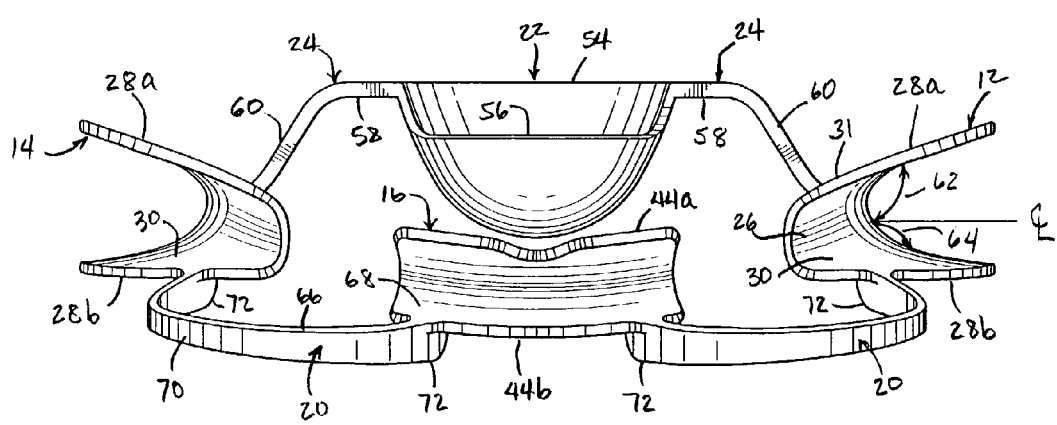
FIG. 3 depicts a semi-schematic side view of the retractor of FIG. 2 taken along line A—A of FIG. 2.

FIG. 3 is a semi-schematic side view of the retractor of FIG. 2 taken at line A—A. FIG. 3 shows the tongue retainer 22 comprising an upper rim 54 and a lower rim 56. The upper rim 54 is positioned higher relative to the lower rim 56 (i.e., protrude further into the mouth than the lower rim when the retractor is in service) and is integrally molded to the two secondary resilient members 24. Alternatively, the tongue retainer 22 can have two even rims to retain the tongue evenly along the upper and lower surfaces of the tongue.

The two secondary resilient members 24 are shown having a generally horizontal section 58 extending from the upper rim 54 and a sloped section 60 connected to the horizontal section 58 and to the radius of curvature 31 of the two side channel retainers 12, 14. Alternatively, the two secondary resilient members 24 can comprise a single sloped section that connects to both the upper rim and the radius of curvature.

Referring specifically to the right side channel retainer 12, there is shown a channel centerline $C_L$, which divides the channel retainer at approximately the mid-point of the race 26. From the perspective of the centerline $C_L$, it can be observed that the inside side wall 28a is angularly spaced a greater distance 62 than the angular position 64 of the outside side wall 28b. The surface area of the outside side wall 28b is also smaller relative to the inside side wall 28a. Among other things, this offset or non-symmetrical configuration is believed to conform better to the physical characteristics of the cheeks and the lips, which translate to a more comfortable fit when the retractor is in service. In other words, the channel retainers 12, 14 shown are not half-circles or symmetrical about a line or a point to accommodate the non-symmetrical features of the lips. However, it is possible to make the side channel retainers 12, 14 symmetrical and oversized and still provide a comfortable fit.

Also shown in FIG. 3 is the manner in which the resilient members 20 are integrally molded to the outside side surface 28b of the side channel retainers 12, 14 and the outside side surface 44b of the lip channel retainer 16. In particular, in one embodiment, the resilient members 20 each has an upper edge 66 that is flushed, flat, or otherwise smoothly transitioned with the interior surface 30 of the side channel retainers 12, 14 and the interior surface 68 of the lip channel retainer 16. This arrangement allows the retractor 10 to be worn without sharp edges projecting or protruding against the inside surface of the lips and the cheeks. However, a slight deviation in the transition between the upper edge 66 and the interior surfaces 30, 68 of the channel retainers 12, 14, 16 may still be acceptable as the lips and the cheeks are pliable and can accommodate any minor deviation without over irritating the user/patient.

Referring again to the resilient members 20 (FIG. 3), in one embodiment, the resilient members each comprises a narrow mid-point 70 and two wide end points 72 relative to the mid-point. The end points 72 can also vary in widths or have the same width as compared to the other end points. In such an arrangement, the biasing force 52 (FIG. 2) of the resilient members 20 may be regulated by the width of the mid-point 70 relative to the end points 72. As readily apparent to a person of ordinary skill in the art, the wider the mid-point 70, the more resistant it is to bending, which translate to more biasing force. Thus, the retracting force 52 of the retractor 10 in retracting the cheeks and the lips can vary by varying the width of the mid-point 70. The retracting force can also vary by changing the mechanical properties of the resilient member, such as introducing a mixture of polymers or other thermoplastics into the base material (i.e., a compound).

Figure 4:
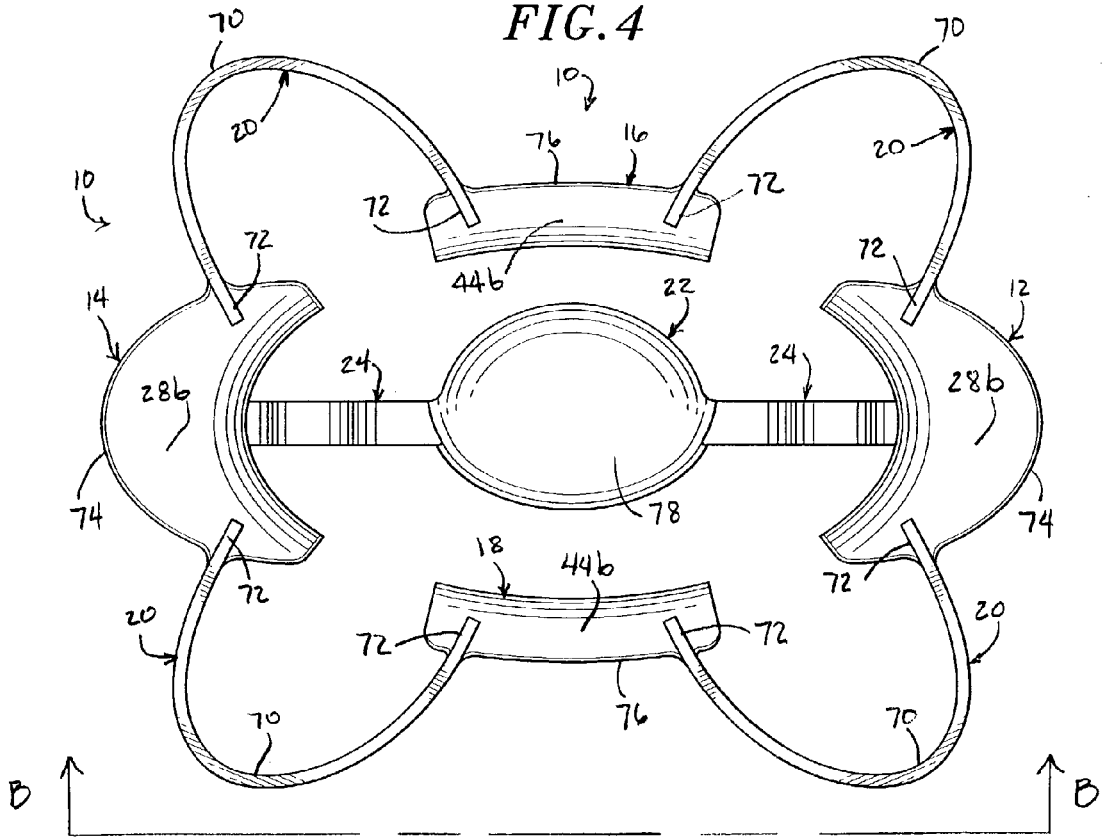
FIG. 4 depicts a semi-schematic top plan view of the retractor of FIG. 1.

Referring now to FIG. 4, there is shown an exemplary semi-schematic top plan view of the retractor of FIG. 1. As shown, the end points 72 of the resilient members 20 extend past the edges 74 of the side channel retainers 12, 14 and the edges 76 of the lip channel retainers 16, 18 for bonding or molding integrity between the resilient members 20 and the channel retainers 12, 14, 16, 18. However, the amount overlap between the end points 72 and the edges can vary depending on the particular materials used for molding the retractor 10, which may have sufficient strength without substantial or any overlapping. The tongue retainer 22 is shown having an oval shaped contour and a smooth exterior surface 78. However, a circular, square, rectangular, or other geometrical shape tongue retainer 22 may also be used without deviating from the scope of the present invention.

Figure 5:
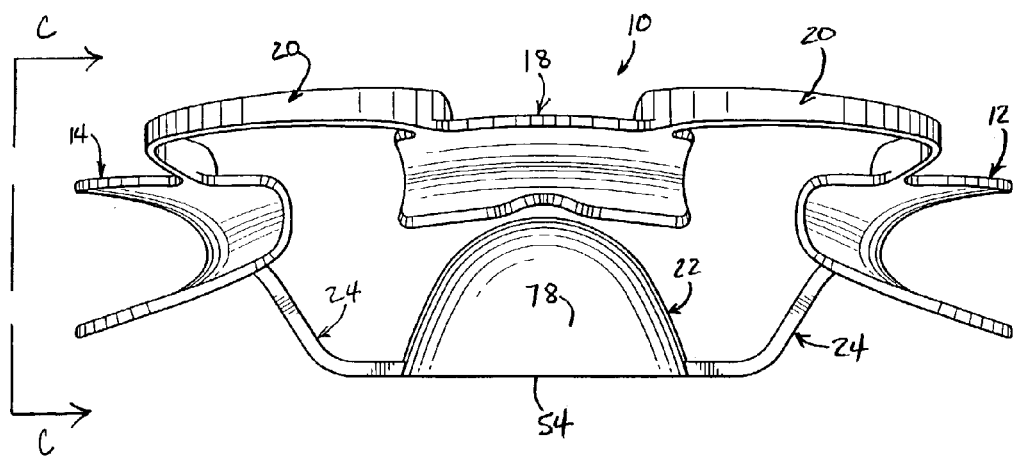
FIG. 5 depicts a semi-schematic side view of the retractor of FIG. 4 taken along line B—B of FIG. 4.

FIG. 5 is a semi-schematic side view of the retractor of FIG. 4 taken at line B—B. Assuming that the side channel retainers 12, 14, and the lip channel retainers 16, 18 define a curved plane, as shown, the upper rim 54 of the tongue retainer 22 is subjacent to the curved plane. As previously discussed, the subjacent configuration and the depth of the trough 23 (FIG. 2) enable the tongue retainer 22 to limit the tongue and retains the tongue in the back of the mouth to further expose the lingual surface of the teeth.

Figure 6:
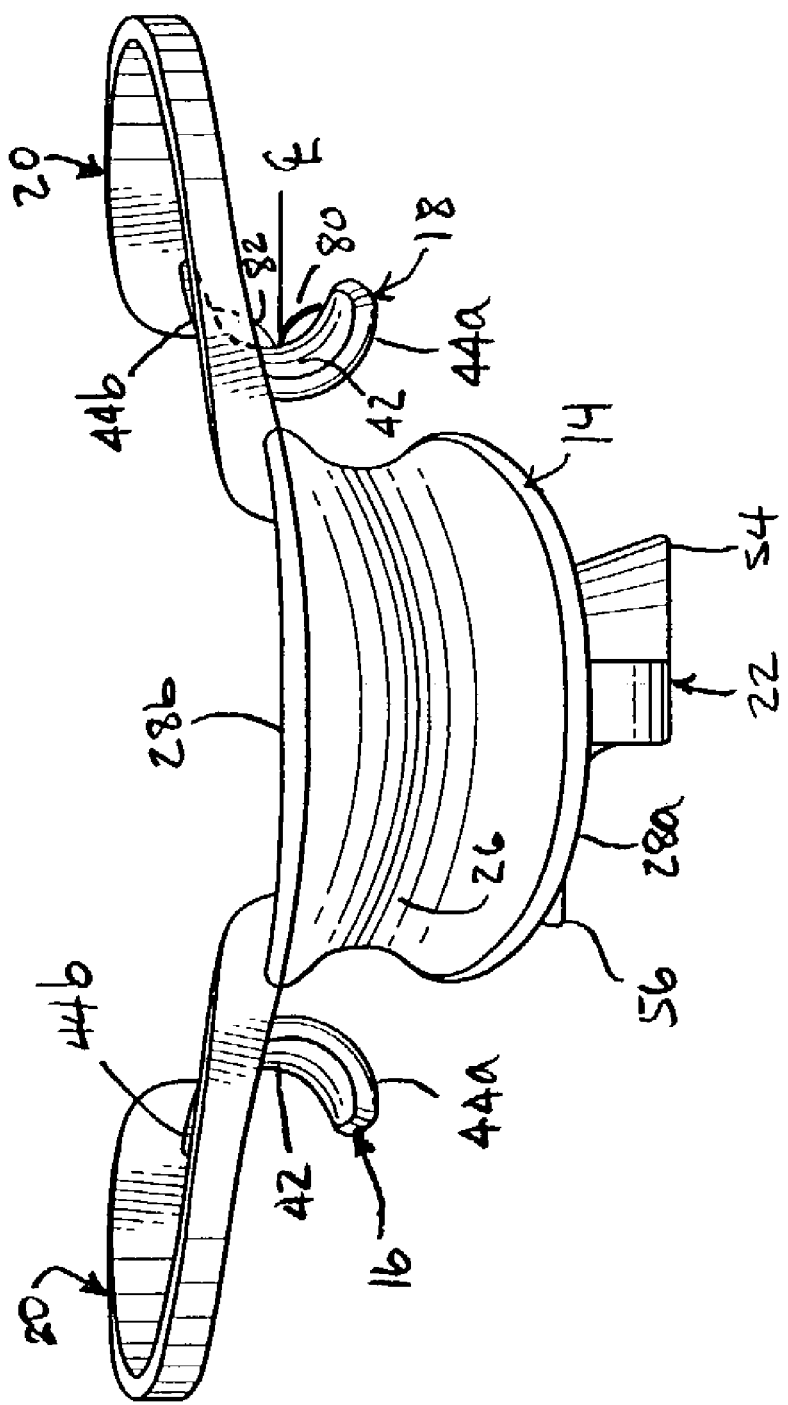
FIG. 6 depicts a semi-schematic side view of the retractor of FIG. 5 taken along line C—C of FIG. 5.

FIG. 6 is a semi-schematic side view of the retractor 10 of FIG. 5 taken at line C—C. Similar to the side channel retainer 12 of FIG. 3, the lip channel retainer 18 comprises a lip channel centerline ℄ (or mid-point, which divides the lip channel retainer at approximately the centerline of the arcuate race 42. From the perspective of the centerline ℄, it can be observed that the inside side wall 44a is angularly spaced a smaller distance 80 than the angular position 82 of the outside side wall 82 relative to the centerline. Among other things, this offset or non-symmetrical configuration is adapted to conform to the physical nature of the lips, which translate to a more comfortable fit when the retractor is in service. Alternatively, the particular relationship may switch such that the angular positions of the inside and outside walls 44a, 44b relative to the centerline are the same or reversed, as discussed above for the side channel retainers 12, 14.

Figure 7:
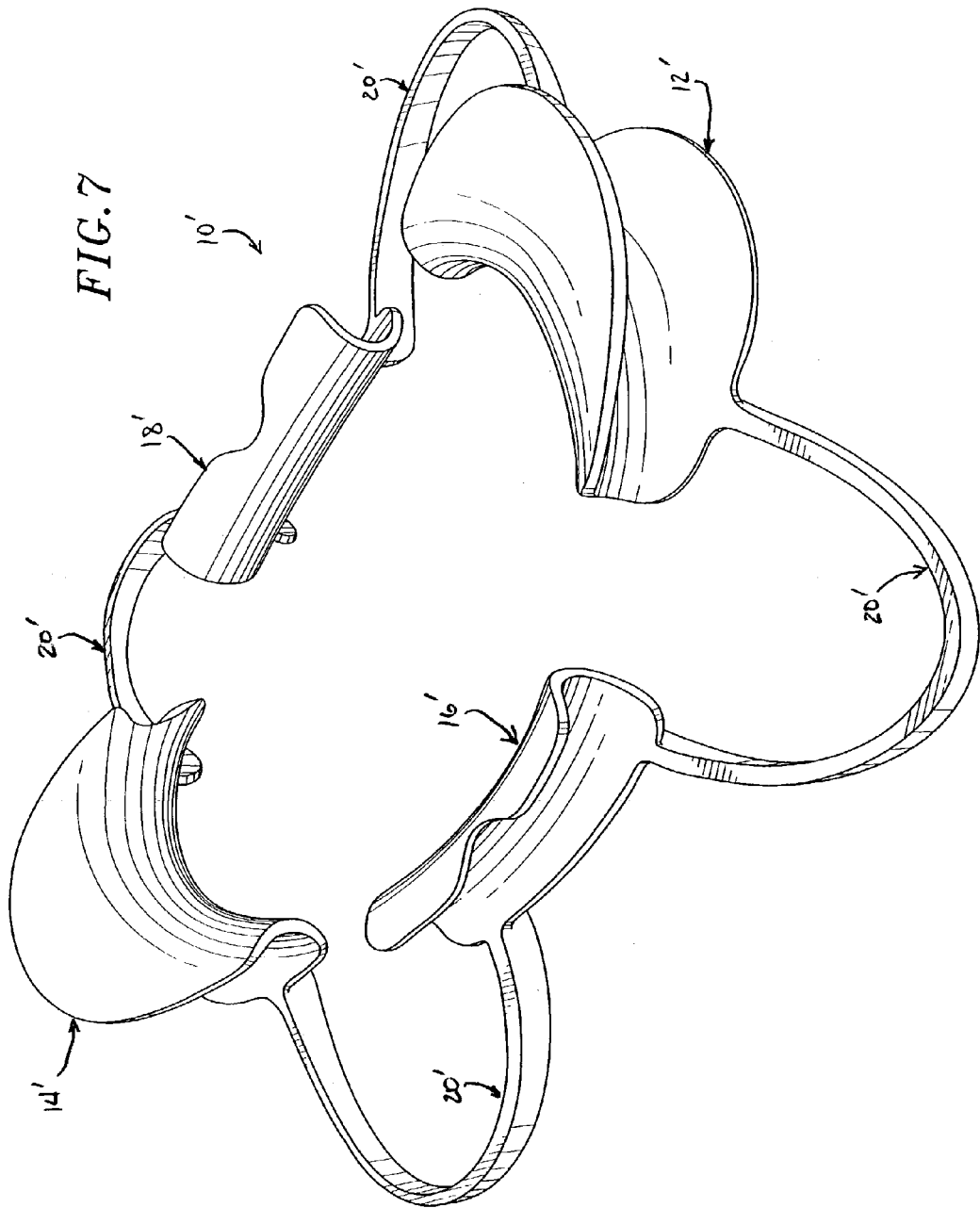
FIG. 7 depicts a semi-schematic perspective view of an alternative retractor provided in accordance to another embodiment of the present invention.

FIG. 7 is a semi-schematic perspective view of an alternative retractor 10' provided in accordance to another embodiment of the present invention. As shown, the retractor comprises two side channel retainers 12', 14' two lip channel retainers 16', 18', and four resilient members 20'. In one embodiment, the alternative retractor 10' is identical to the retractor 10 shown in FIGS. 1–6 except that the alternative retractor 10' does not comprise a tongue retainer. Accordingly, the description set forth above for the retractor 10 applies for the alternative retractor 10' less the tongue retainer.

Figure 8:
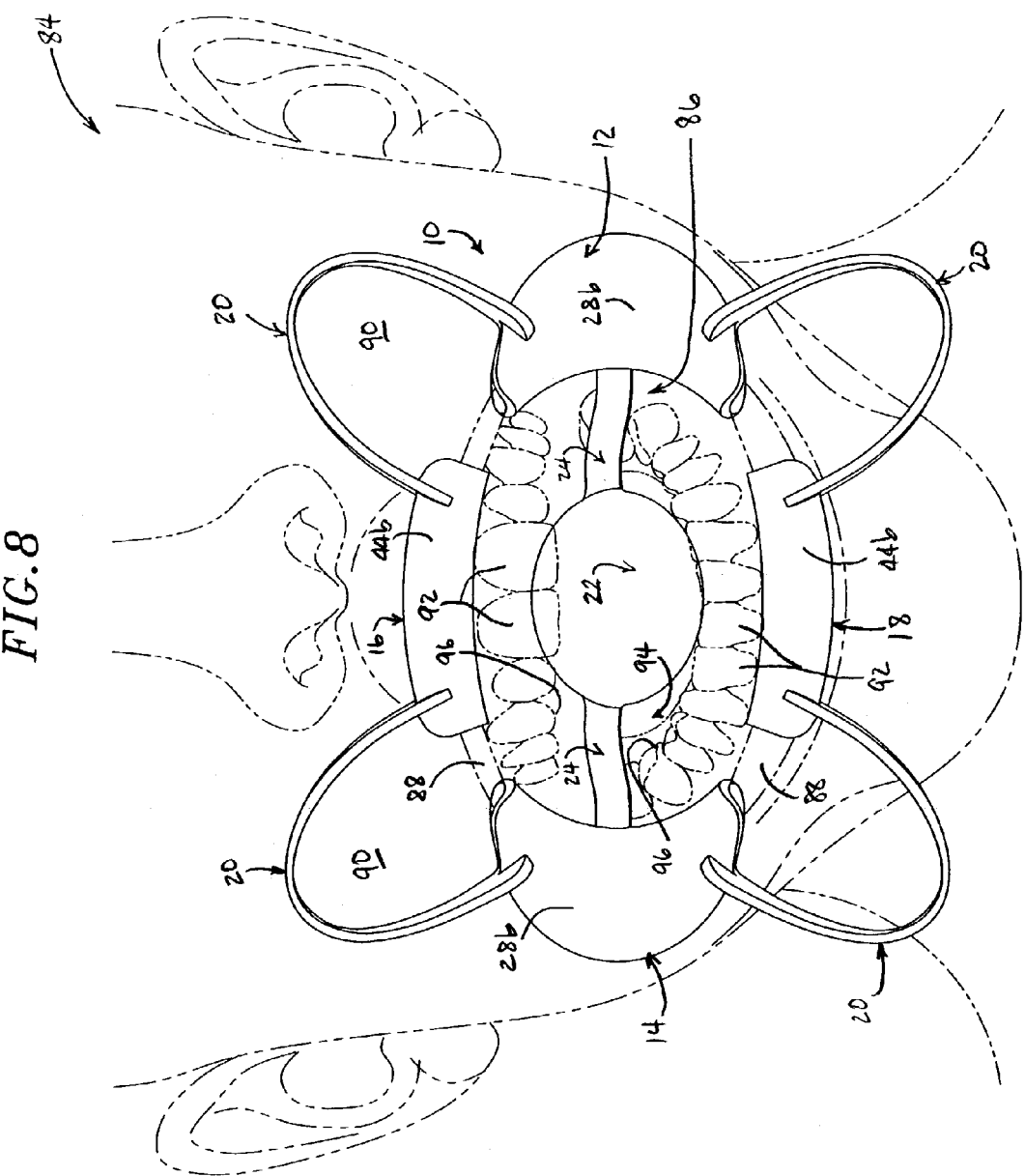
FIG. 8 depicts a semi-schematic front view of the retractor of FIG. 1 in service on a user/patient.

FIG. 8 is an exemplary semi-schematic top plan view of the retractor 10 of FIG. 1 in use on a patient or user 84. As shown, the retractor 10 engages the user's mouth 86 to retract the user's lips 88 and cheeks 90. Once in position, the user's mouth 86, and particularly the teeth 92, is exposed for examination and/or treatment by a health care professional. More specifically, the side channel retainers 12, 14 engage the side of the mouth, the lip channel retainers 16, 18 engage the upper and lower lips 88, and the resilient members 20 bias the four channel retainers, which bias the lips 88 and cheeks 90 open, to expose the teeth and the inside of the mouth 86. In the retractor used position, the outside side walls 28a, 44a and the resilient members 20 are exposed extraorally of the mouth.

The tongue retainer 22 is shown engaged to the tongue 94 and relegates the tongue to the back region of the mouth 86. When incorporated, the tongue retainer 22 is configured to further expose the lingual surface 96 of the teeth for examination and/or treatment.

The retractor 10 may be installed on the lips 88 by first placing the upper lip over the inside side wall 44a and into the race 42 of the upper lip channel retainer 16. The two side channel retainers 12, 14 are then squeezed together and placed into the mouth, either concurrently or one at the time, until the sides of the lips fit over the inside side walls 28a of the side channel retainers 12, 14 and into the race 26. Finally, the lower lip channel retainer 18 is squeezed and placed over the lower lip 88 with the lower lip engaging the race 42 of the lip channel retainer 18. Once installed, the tongue retainer 22 automatically aligns with the tongue 94 to block the tongue from maneuverability. The retractor 10 may also be installed by reversing the steps discussed above or squeezing all four channel retainers at the same time and fitting the lips over the channel retainers.

Figure 9:
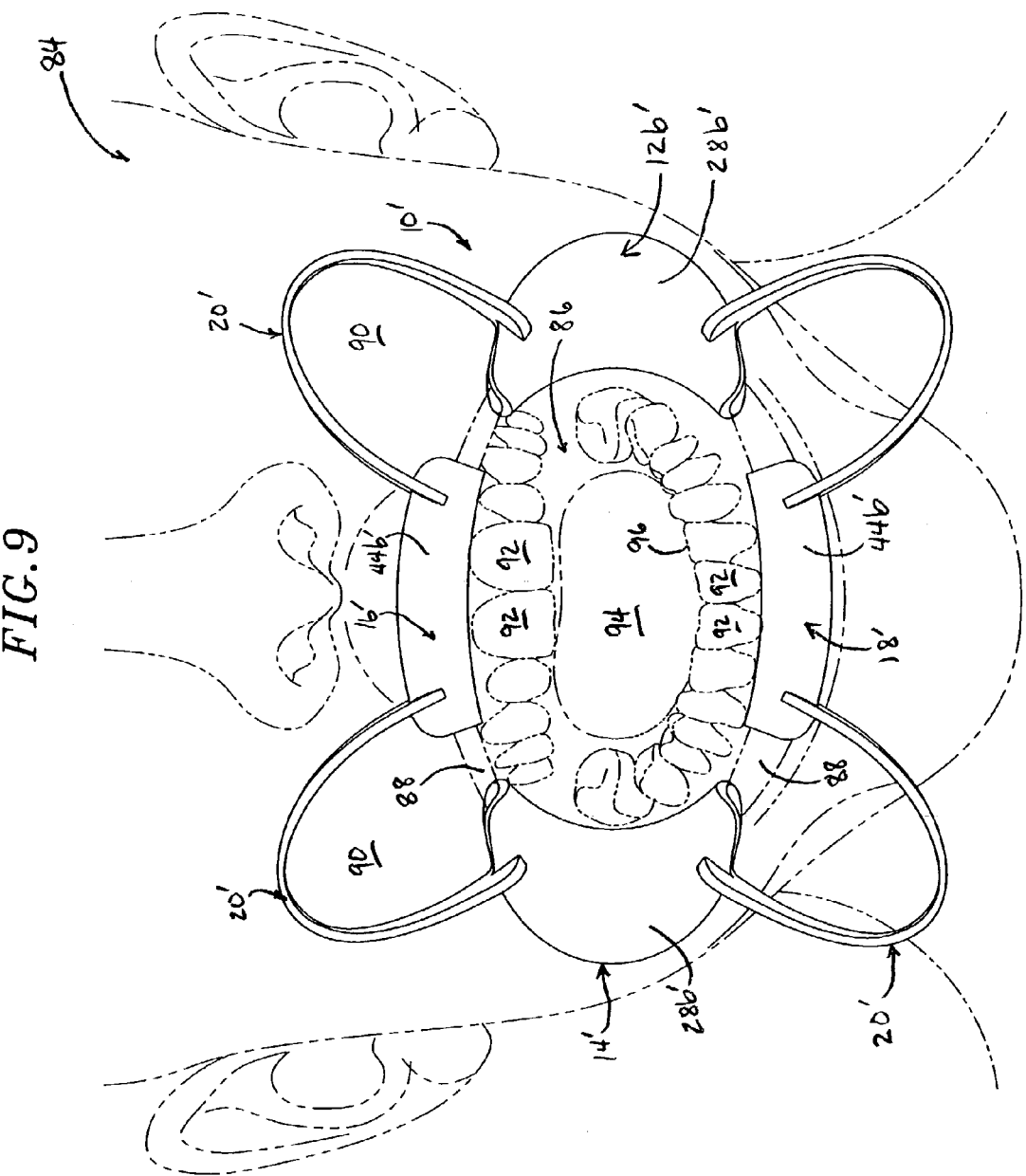
FIG. 9 depicts a semi-schematic front view of the retractor of FIG. 7 in service on a user/patient.

FIG. 9 is an exemplary semi-schematic top plan view of the alternative retractor 10' of FIG. 7 in use on a patient or user 84. Like the retractor 10 in FIG. 8, the alternative retractor 10' engages the lips to retract the lips 88 and the cheeks 90 to thereby expose the teeth 92 for examination and/or treatment. However, unlike the retractor 10 of FIG. 8, the alternative retractor 10' does not incorporate a tongue retainer. Thus, the tongue 94 is shown free to move within the oral cavity of the mouth 86.

Although the preferred embodiments of the invention have been described with some specificity, the description and drawings set forth herein are not intended to be delimiting, and persons of ordinary skill in the art will understand that various modifications may be made to the embodiments discussed herein without departing from the scope of the invention, and all such changes and modifications are intended to be encompassed within the appended claims. Various changes to the retractor may be made including manufacturing the dimensions differently, using different materials, making the retractor opaque, semi-opaque, transparent, colored, having a textured finish, etc. For example, instead of making the retractor by a single step injection molding, the retractor can be made by welding the various components together, and using multiple molding steps. Also, the four channel retainers can be arranged such that two of the retainers cup two ends of the upper lip and two of the other retainers cup two ends of the lower lip. This alternative retractor can also be incorporated with or without a tongue retainer. Accordingly, many alterations and modifications may be made by those having ordinary skill in the art without deviating from the spirit and scope of the invention.

What is claimed is:

1. A retractor for retracting a user's lips comprising four channel retainers and four members, wherein each channel retainer comprises a race, an inside side wall, and an outside side wall, and wherein each resilient member is integrally molded to two outside walls of two adjacent channel retainers and comprises an arch.

2. The retractor of claim 1, further comprising a frenum release on at least one of the inside side walls of the four channel retainers.

3. The retractor of claim 1, wherein the race of each of the four channel retainers comprises a radius of curvature.

4. The retractor of claim 1, wherein the four channel retainers comprise two side channel retainers and two-lip channel retainers, and wherein the inside side walls of the side channel retainers are larger than the outside side walls of the side channel retainers.

5. The retractor of claim 1, wherein the retractor is made from polypropylene.

6. The retractor of claim 1, wherein the four channel retainers and the four resilient members are integrally molded.

7. The retractor of claim 1, wherein the four resilient members each comprises a mid-point and two end points, and wherein the mid-point is narrower than the two end points.

8. The retractor of claim 1, wherein the four channel retainers each comprises an inside surface and the four resilient members each comprises an upper edge, and wherein the upper edge of the resilient member is substantially planar with the inside surface of the channel retainer.

9. The retractor of claim 1, wherein the race of each channel retainers comprises a centerline, and wherein the inside side wall and the outside side wall is non-symmetrical with respect to the centerline.

10. The retractor of claim 1, wherein the four channel retainers comprise two lip channel retainers, and wherein the inside walls of the lip channel retainers each comprises a frenum release.

11. The retractor of claim 1, further comprising a tongue retainer and wherein the tongue retainer is attached to two of the channel retainers by two secondary resilient members.

12. The retractor of claim 11, wherein the retractor is made from polypropylene.

13. The retractor of claim 11, wherein at least one of the four channel retainers comprises a frenum release.

14. The retractor of claim 11, wherein the secondary resilient members each comprises a sloped section.

15. The retractor of claim 1, further comprising a tongue retainer comprising a trough for accommodating a tongue.

16. A retractor a user's lips comprising four channel retainers coupled to four resilient members, the four channel retainers each comprises a arcuate race defined by two side walls, wherein the side walls of two of the four channel retainers are larger in dimension than the side walls of the remaining two channel retainers.

17. The retractor of claim 16, further comprising a frenum release on at least one of the side walls of the four channel retainers.

18. The retractor of claim 16, wherein the race of each of the four channel retainers comprises a radius of curvature.

19. The retractor of claim 16, wherein the four channel retainers comprise two side channel retainers and two lip channel retainers, and wherein the side walls of the side channel retainers are larger than the side walls of the side channel retainers.

20. The retractor of claim 16, wherein the retractor is made from polypropylene.

21. The retractor of claim 16, further comprising a tongue retainer and wherein the tongue retainer is attached to two of the channel retainers by two secondary resilient members.

* * * * *

UNITED STATES PATENT AND TRADEMARK OFFICE
CERTIFICATE OF CORRECTION

PATENT NO. : 6,923,761 B1
DATED : August 2, 2005
INVENTOR(S) : Dorfman

It is certified that error appears in the above-identified patent and that said Letters Patent is hereby corrected as shown below:

<u>Column 7,</u>
Line 13, after "four", insert -- resilient --.
Line 16, after "outside", insert -- side --.
Line 24, delete "two-lip", insert -- two lip --.

<u>Column 8,</u>
Line 1, delete "is", insert -- are --.
Line 5, after "inside", insert -- side --.
Line 18, after "A retractor", insert -- for retracting --.
Line 20, delete "a arcuate", insert --an arcuate --.

Signed and Sealed this

Twenty-first Day of March, 2006

JON W. DUDAS
*Director of the United States Patent and Trademark Office*